(12) United States Patent
Vidyasagar et al.

(10) Patent No.: US 10,502,731 B2
(45) Date of Patent: *Dec. 10, 2019

(54) USE OF ANOCTAMIN AS A BIOMARKER FOR RADIATION BIODOSIMETRY

(71) Applicant: University of Florida Research Foundation, Incorporated, Gainesville, FL (US)

(72) Inventors: Sadasivan Vidyasagar, Gainesville, FL (US); Paul Okunieff, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,923

(22) Filed: Nov. 27, 2017

(65) Prior Publication Data

US 2018/0074048 A1 Mar. 15, 2018

Related U.S. Application Data

(63) Continuation of application No. 14/406,087, filed as application No. PCT/US2013/063695 on Oct. 7, 2013, now Pat. No. 9,829,484.

(60) Provisional application No. 61/710,413, filed on Oct. 5, 2012.

(51) Int. Cl.
| | |
|---|---|
| *C12Q 1/68* | (2018.01) |
| *G01N 33/543* | (2006.01) |
| *G01N 33/68* | (2006.01) |
| *C12Q 1/6883* | (2018.01) |

(52) U.S. Cl.
CPC ..... *G01N 33/54306* (2013.01); *C12Q 1/6883* (2013.01); *G01N 33/6893* (2013.01); *C12Q 2600/158* (2013.01); *G01N 2333/705* (2013.01); *G01N 2500/10* (2013.01); *G01N 2800/40* (2013.01)

(58) Field of Classification Search
None
See application file for complete search history.

(56) References Cited

U.S. PATENT DOCUMENTS

| | | | |
|---|---|---|---|
| 7,201,931 | B2 | 4/2007 | Di Pierro |
| 9,829,484 | B2 * | 11/2017 | Vidyasagar .......... C12Q 1/6883 |
| 2009/0318556 | A1 | 12/2009 | Idle et al. |
| 2012/0058088 | A1 | 3/2012 | Sardi |

FOREIGN PATENT DOCUMENTS

| | | |
|---|---|---|
| EP | 1414473 B1 | 3/2006 |
| WO | 2011127056 A2 | 10/2011 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Cho, H. et al., "The calcium-activated chloride channel anoctamin 1 acts as a heat sensor in nociceptive neurons." Nature Neuroscience, Jul. 2012, 15 (7): 1015-1022.
Cobb, J. P. et al., "Sepsis gene expression profiling: Murine splenic compared with hepatic responses determined by using complementary DNA microarrays." Crit. Care. Med., Dec. 2002, 30 (12): 2711-2721.
Cui, W. et al., "Plasma miRNA as Biomarkers for Assessment of Total-Body Radiation Exposure Dosimetry." PLoS ONE, Aug. 2011, 6 (8): 1-12, e22988.
Enard, W. et al., "Intra- and Interspecific Variation in Primate Gene Expression Patterns." Science, Apr. 2002, 296: 340-343.
Marchetti, F et al., "Candidate protein biodosimeters of human exposure to ionizing radiation." Int. J. Radiat. Biol, Sep. 2006, 82 (9): 605-639.
Ménard, C. et al., "Discovering Clinical Biomarkers of Ionizing Radiation Exposure with Serum Proteomic Analysis." Cancer Res., Feb. 2006, 66 (3): 1844-1850.

* cited by examiner

*Primary Examiner* — Katherine D Salmon
(74) *Attorney, Agent, or Firm* — Saliwanchik, Lloyd & Eisenschenk

(57) ABSTRACT

In one embodiment, the present invention pertains to the use of anoctamin as a biomarker for determining radiation dosimetery. In certain embodiments, the present invention relates to the use of anoctamin as a biomarker for diagnosing the presence of radiation toxicity in a subject who has been exposed to ionizing radiation, as well as for determining the absorbed radiation dose in a subject who has been exposed to a known or unknown dose of ionizing radiation. In another embodiment, the expression level of anoctamin can be used as a secondary endpoint to determine mechanisms of action and/or pharmacodynamic (PD) effects of an agent for reducing radiation toxicity.

1 Claim, 14 Drawing Sheets

Specification includes a Sequence Listing.

Ano 1 3Gy+6d

Ano1 7Gy+6d

Ano1 7Gy+6d

```
                         SEQUENCE LISTING

<160> NUMBER OF SEQ ID NOS: 2

<210> SEQ ID NO 1
<211> LENGTH: 986
<212> TYPE: PRT
<213> ORGANISM: Homo sapiens

<400> SEQUENCE: 1

Met Arg Val Asn Glu Lys Tyr Ser Thr Leu Pro Ala Glu Asp Arg Ser
1               5                   10                  15

Val His Ile Ile Asn Ile Cys Ala Ile Glu Asp Ile Gly Tyr Leu Pro
            20                  25                  30

Ser Glu Gly Thr Leu Leu Asn Ser Leu Ser Val Asp Pro Asp Ala Glu
        35                  40                  45

Cys Lys Tyr Gly Leu Tyr Phe Arg Asp Gly Arg Arg Lys Val Asp Tyr
    50                  55                  60

Ile Leu Val Tyr His His Lys Arg Pro Ser Gly Asn Arg Thr Leu Val
65                  70                  75                  80

Arg Arg Val Gln His Ser Asp Thr Pro Ser Gly Ala Arg Ser Val Lys
                85                  90                  95

Gln Asp His Pro Leu Pro Gly Lys Gly Ala Ser Leu Asp Ala Gly Ser
            100                 105                 110

Gly Glu Pro Pro Met Asp Tyr His Glu Asp Asp Lys Arg Phe Arg Arg
        115                 120                 125

Glu Glu Tyr Glu Gly Asn Leu Leu Glu Ala Gly Leu Glu Leu Glu Arg
    130                 135                 140

Asp Glu Asp Thr Lys Ile His Gly Val Gly Phe Val Lys Ile His Ala
145                 150                 155                 160

Pro Trp Asn Val Leu Cys Arg Glu Ala Glu Phe Leu Lys Leu Lys Met
                165                 170                 175

Pro Thr Lys Lys Met Tyr His Ile Asn Glu Thr Arg Gly Leu Leu Lys
            180                 185                 190

Lys Ile Asn Ser Val Leu Gln Lys Ile Thr Asp Pro Ile Gln Pro Lys
        195                 200                 205

Val Ala Glu His Arg Pro Gln Thr Met Lys Arg Leu Ser Tyr Pro Phe
    210                 215                 220

Ser Arg Glu Lys Gln His Leu Phe Asp Leu Ser Asp Lys Asp Ser Phe
225                 230                 235                 240

Phe Asp Ser Lys Thr Arg Ser Thr Ile Val Tyr Glu Ile Leu Lys Arg
                245                 250                 255
```

```
Thr Thr Cys Thr Lys Ala Lys Tyr Ser Met Gly Ile Thr Ser Leu Leu
            260                 265                 270

Ala Asn Gly Val Tyr Ala Ala Tyr Pro Leu His Asp Gly Asp Tyr
        275                 280                 285

Asn Gly Glu Asn Val Glu Phe Asn Asp Arg Lys Leu Leu Tyr Glu Glu
    290                 295                 300

Trp Ala Arg Tyr Gly Val Phe Tyr Lys Tyr Gln Pro Ile Asp Leu Val
305                 310                 315                 320

Arg Lys Tyr Phe Gly Glu Lys Ile Gly Leu Tyr Phe Ala Trp Leu Gly
                325                 330                 335

Val Tyr Thr Gln Met Leu Ile Pro Ala Ser Ile Val Gly Ile Ile Val
            340                 345                 350

Phe Leu Tyr Gly Cys Ala Thr Met Asp Glu Asn Ile Pro Ser Met Glu
            355                 360                 365

Met Cys Asp Gln Arg His Asn Ile Thr Met Cys Pro Leu Cys Asp Lys
    370                 375                 380

Thr Cys Ser Tyr Trp Lys Met Ser Ser Ala Cys Ala Thr Ala Arg Ala
385                 390                 395                 400

Ser His Leu Phe Asp Asn Pro Ala Thr Val Phe Phe Ser Val Phe Met
                405                 410                 415

Ala Leu Trp Ala Ala Thr Phe Met Glu His Trp Lys Arg Lys Gln Met
            420                 425                 430

Arg Leu Asn Tyr Arg Trp Asp Leu Thr Gly Phe Glu Glu Glu Glu
            435                 440                 445

Ala Val Lys Asp His Pro Arg Ala Glu Tyr Glu Ala Arg Val Leu Glu
    450                 455                 460

Lys Ser Leu Lys Lys Glu Ser Arg Asn Lys Glu Lys Arg Arg His Ile
465                 470                 475                 480

Pro Glu Glu Ser Thr Asn Lys Trp Lys Gln Arg Val Lys Thr Ala Met
                485                 490                 495

Ala Gly Val Lys Leu Thr Asp Lys Val Lys Leu Thr Trp Arg Asp Arg
            500                 505                 510

Phe Pro Ala Tyr Leu Thr Asn Leu Val Ser Ile Ile Phe Met Ile Ala
            515                 520                 525

Val Thr Phe Ala Ile Val Leu Gly Val Ile Ile Tyr Arg Ile Ser Met
    530                 535                 540

Ala Ala Ala Leu Ala Met Asn Ser Ser Pro Ser Val Arg Ser Asn Ile
545                 550                 555                 560

Arg Val Thr Val Thr Ala Thr Ala Val Ile Ile Asn Leu Val Val Ile
                565                 570                 575

Ile Leu Leu Asp Glu Val Tyr Gly Cys Ile Ala Arg Trp Leu Thr Lys
            580                 585                 590

Ile Glu Val Pro Lys Thr Glu Lys Ser Phe Glu Glu Arg Leu Ile Phe
            595                 600                 605

Lys Ala Phe Leu Leu Lys Phe Val Asn Ser Tyr Thr Pro Ile Phe Tyr
    610                 615                 620

Val Ala Phe Phe Lys Gly Arg Phe Val Gly Arg Pro Gly Asp Tyr Val
625                 630                 635                 640

Tyr Ile Phe Arg Ser Phe Arg Met Glu Glu Cys Ala Pro Gly Gly Cys
                645                 650                 655

Leu Met Glu Leu Cys Ile Gln Leu Ser Ile Ile Met Leu Gly Lys Gln
            660                 665                 670

Leu Ile Gln Asn Asn Leu Phe Glu Ile Gly Ile Pro Lys Met Lys Lys
```

```
                675                 680                 685

Leu Ile Arg Tyr Leu Lys Leu Lys Gln Gln Ser Pro Pro Asp His Glu
690                 695                 700

Glu Cys Val Lys Arg Lys Gln Arg Tyr Glu Val Asp Tyr Asn Leu Glu
705                 710                 715                 720

Pro Phe Ala Gly Leu Thr Pro Glu Tyr Met Glu Met Ile Ile Gln Phe
                725                 730                 735

Gly Phe Val Thr Leu Phe Val Ala Ser Phe Pro Leu Ala Pro Leu Phe
                740                 745                 750

Ala Leu Leu Asn Asn Ile Ile Glu Ile Arg Leu Asp Ala Lys Lys Phe
            755                 760                 765

Val Thr Glu Leu Arg Arg Pro Val Ala Val Arg Ala Lys Asp Ile Gly
770                 775                 780

Ile Trp Tyr Asn Ile Leu Arg Gly Ile Gly Lys Leu Ala Val Ile Ile
785                 790                 795                 800

Asn Ala Phe Val Ile Ser Phe Thr Ser Asp Phe Ile Pro Arg Leu Val
                805                 810                 815

Tyr Leu Tyr Met Tyr Ser Lys Asn Gly Thr Met His Gly Phe Val Asn
                820                 825                 830

His Thr Leu Ser Ser Phe Asn Val Ser Asp Phe Gln Asn Gly Thr Ala
            835                 840                 845

Pro Asn Asp Pro Leu Asp Leu Gly Tyr Glu Val Gln Ile Cys Arg Tyr
850                 855                 860

Lys Asp Tyr Arg Glu Pro Pro Trp Ser Glu Asn Lys Tyr Asp Ile Ser
865                 870                 875                 880

Lys Asp Phe Trp Ala Val Leu Ala Ala Arg Leu Ala Phe Val Ile Val
                885                 890                 895

Phe Gln Asn Leu Val Met Phe Met Ser Asp Phe Val Asp Trp Val Ile
                900                 905                 910

Pro Asp Ile Pro Lys Asp Ile Ser Gln Gln Ile His Lys Glu Lys Val
            915                 920                 925

Leu Met Val Glu Leu Phe Met Arg Glu Glu Gln Asp Lys Gln Gln Leu
930                 935                 940

Leu Glu Thr Trp Met Glu Lys Glu Arg Gln Lys Asp Glu Pro Pro Cys
945                 950                 955                 960

Asn His His Asn Thr Lys Ala Cys Pro Asp Ser Leu Gly Ser Pro Ala
                965                 970                 975

Pro Ser His Ala Tyr His Gly Gly Val Leu
            980                 985

<210> SEQ ID NO 2
<211> LENGTH: 4811
<212> TYPE: DNA
<213> ORGANISM: Homo sapiens

<400> SEQUENCE: 2
aaaggcgggc cggctggcgt ccaagttcct gaccaggcgc gggccggccc gcgggaccag      60
cagccgggtg gcggcgcgat cggccccgag aggctcaggc gccccccgca tcgagcgcgc     120
gggccgggcg ggccagggcg gcgggcggag cgggaggcgc ccacgtcccc ggcgggcctg     180
ggcgcgggga ggcccggccc cctgcgagcg cgccgcgaac gctgcggtct ccgcccgcag     240
aggccgccgg ggccgtggat ggggagggcg cgccgcccgg cggtcccagc gcacaggcgg     300
ccacgatgag ggtcaacgag aagtactcga cgctcccggc cgaggaccgc agcgtccaca     360
```

```
tcatcaacat ctgcgccatc gaggacatcg gctacctgcc gtccgagggc acgctgctga     420
actccttatc tgtggaccct gatgccgagt gcaagtatgg cctgtacttc agggacggcc     480
ggcgcaaggt ggactacatc ctggtgtacc atcacaagag gccctcgggc aaccggaccc     540
tggtcaggag ggtgcagcac agcgacaccc cctctgggc tcgcagcgtc aagcaggacc      600
accccctgcc gggcaagggg gcgtcgctgg atgcaggctc gggggagccc ccgatggact     660
accacgagga tgacaagcgc ttccgcaggg aggagtacga gggcaacctc ctggaggcgg     720
gcctggagct ggagcgggac gaggacacta aaatccacgg agtcgggttt gtgaaaatcc     780 atgcccctg gaacgtgctg tgcagagagg ccgagtttct gaaactgaag atgccgacga      840
agaagatgta ccacattaat gagacccgtg gcctcctgaa aaaaatcaac tctgtgctcc     900
agaaaatcac agatcccatc cagcccaaag tggctgagca caggcccag accatgaaga     960 gactctccta tcccttctcc cgggagaagc agcatctatt tgacttgtct gataaggatt    1020 ccttttcga cagcaaaacc cggagcacga ttgtctatga gatcttgaag gaacgacgt      1080 gtacaaaggc caagtacagc atgggcatca cgagcctgct ggccaatggt gtgtacgcgg    1140
ctgcataccc actgcacgat ggagactaca acggtgaaaa cgtcgagttc aacgacagaa    1200
aactcctgta cgaagagtgg gcacgctatg gagttttcta taagtaccag cccatcgacc    1260
tggtcaggaa gtattttggg gagaagatcg gcctgtactt cgcctggctg ggcgtgtaca    1320
cccagatgct catccctgcc tccatcgtgg gaatcattgt cttcctgtac ggatgcgcca    1380
ccatggatga aaacatcccc agcatggaga tgtgtgacca gagacacaat atcaccatgt    1440
gcccgctttg cgacaagacc tgcagctact ggaagatgag ctcagcctgc gccacggccc    1500
gcgccagcca cctcttcgac aaccccgcca cggtcttctt ctctgtcttc atggccctct    1560
gggctgccac cttcatggag cactggaagc ggaaacagat gcgactcaac taccgctggg    1620
acctcacggg ctttgaagag aagaggagg ctgtcaagga tcatcctaga gctgaatacg     1680
aagccagagt cttggagaag tctctgaaga aagagtccag aaacaaagag aagcgccggc    1740
atattccaga ggagtcaaca aacaaatgga agcagagggt taagacagcc atggcggggg    1800
tgaaattgac tgacaaagtg aagctgacat ggagagatcg gttcccagcc tacctcacta    1860
acttggtctc catcatcttc atgattgcag tgacgtttgc catcgtcctc ggcgtcatca    1920
tctacagaat ctccatggcc gccgccttgg ccatgaactc ctccccctcc gtgcggtcca    1980
acatccgggt cacagtcaca gccaccgcag tcatcatcaa cctagtggtc atcatcctcc    2040
tggacgaggt gtatggctgc atagcccgat ggctcaccaa gatcgaggtc ccaaagacgg    2100
agaaaagctt tgaggagagg ctgatcttca aggctttcct gctgaagttt gtgaattcct    2160
acacccccat ctttttacgtg gcgttcttca aaggccggtt tgttggacgc ccgggcgact    2220
acgtgtacat tttccgttcc ttccgaatgg aagagtgtgc gccaggggc tgcctgatgg     2280 agctatgcat ccagctcagc atcatcatgc tggggaaaca gctgatccag aacaacctgt    2340
tcgagatcgg catcccgaag atgaagaagc tcatccgcta cctgaagctg aagcagcaga    2400
gcccccctga ccacgaggag tgtgtgaaga ggaaacagcg gtacgaggtg gattacaacc    2460
tggagccctt cgcgggcctc accccagagt acatggaaat gatcatccag tttggcttcg    2520
tcaccctgtt tgtcgcctcc ttccccctgg ccccactgtt tgcgctgctg aacaacatca    2580
tcgagatccg cctggacgcc aaaaagtttg tcactgagct ccgaaggccg gtagctgtca    2640
gagccaaaga catcggaatc tggtacaata tcctcagagg cattgggaag cttgctgtca    2700
tcatcaatgc cttcgtgatc tccttcacgt ctgacttcat cccgcgcctg gtgtacctct    2760
```

```
acatgtacag taagaacggg accatgcacg gcttcgtcaa ccacaccctc tcctccttca   2820
acgtcagtga cttccagaac ggcacggccc ccaatgaccc cctggacctg ggctacgagg   2880
tgcagatctg caggtataaa gactaccgag agccgccgtg gtcggaaaac aagtacgaca   2940
tctccaagga cttctgggcc gtcctggcag cccggctggc gtttgtcatc gtcttccaga   3000
acctggtcat gttcatgagc gactttgtgg actgggtcat cccggacatc cccaaggaca   3060
tcagccagca gatccacaag gagaaggtgc tcatggtgga gctgttcatg cgggaggagc   3120
aagacaagca gcagctgctg gaaacctgga tggagaagga gcggcagaag gacgagccgc   3180
cgtgcaacca ccacaacacc aaagcctgcc cagacagcct cggcagccca gccccagcc    3240 atgcctacca cgggggcgtc ctgtagctat gccagcgggg ctgggcaggc cagccgggca   3300
tcctgaccga tgggcaccct ctcccagggc aggcggcttc ccgctcccac cagggcccgg   3360
tgggtcctgg gttttctgca acatggagg accactttct gataggacat tttcctttct    3420
tctttctgtt ttctttccct tgttttttgca caaagccatt atgcagggaa tattttttaa   3480
tctgtagtat tcaagatgaa tcaaaatgat ggctggtaat acggcaataa ggtagcaaag   3540
gcaggtgctt tgcagaaaga atgcttggaa acttgagtct ccctagaggt gaaaagtgag   3600
cagaggcccg tagaaaccct cctctgaatc ctcctaattc cttaagatag atgcaaaatg   3660
gtaagccgag gcatcgcgca aaagctggtg cgatgcttca gggaaaatgg aaaacccacg   3720
caagaataat gattgattcc ggttccaaaa ggtgtcacct acctgtttca gaaaagttag   3780
actttccatc gccttttcct tccatcagtt gagtggctga gagagaagtg cctcatccct   3840
gagccacaca gggggcgtgg gagcatccca gttatccctg gaaagctaga aggggacaga   3900
ggtgtccctg attaagcagg aaacagcacc cttggcgtcc ccagcaggct ccccactgtc   3960
agccacacac ctgcccccat cacaccaagc cgacctcaga gttgttcatc ttccttatgg   4020
gacaaaaccg gttgaccaga aaatgggcag agagagatga cctcggaagc atttccacag   4080
atggtgtcag ggtttcaaga agtcttaggg cttccagggg tcccctggaa gctttagaat   4140
atttatgggt ttttttttca aatatcaatt atatggtaga ttgaggattt ttttctgta    4200 gctcaaaggt ggagggagtt tattagttaa ccaaatatcg ttgagaggaa tttaaaatac   4260
tgttactacc aaagattttt attaataaag gcttatattt tggtaacact tctctatatt   4320
tttactcaca ggaatgtcac tgttggacaa ttattttaaa agtgtataaa accaagtctc   4380
ataaatgata tgagtgatct aaatttgcag caatgatact aaacaactct ctgaaatttc   4440
tcaagcacca agagaaacat catttttagca aaggccagga ggaaaaatag aaataaattt   4500
gtcttgaaga tctcattgat gtgatgttac attccctta atctgccaac tgtggtcaaa    4560
gttcataggt gtcgtacatt tccattattt gctaaaatca tgcaatctga tgcttctctt   4620
ttctcttgta cagtaagtag tttgaagtgg gttttgtata taaatactgt attaaaaatt   4680
aggcaattac caaaaatcct tttatggaaa ccattttttt aaaaagtgaa tgtacacaaa   4740
tccacagagg actgtggctg gacattcatc taaataaatt tgaatatacg acacttttct   4800
cacttgaaaa a                                                        4811
```

USE OF ANOCTAMIN AS A BIOMARKER FOR RADIATION BIODOSIMETRY

CROSS-REFERENCE TO A RELATED APPLICATION

This application is a continuation of co-pending U.S. application Ser. No. 14/406,087, filed Dec. 5, 2014, which is a U. S. National Stage Application of International Application Number PCT/US2013/063695, filed Oct. 7, 2013, which claims the benefit of U.S. provisional application Ser. No. 61/710,413, filed Oct. 5, 2012, all of which are incorporated herein by reference in their entirety.

The Sequence Listing for this application is labeled "SeqList-07Oct13_ST25.txt", which was created on Oct. 7, 2013, and is 15 KB. The entire content is incorporated herein by reference in its entirety.

BACKGROUND OF INVENTION

Radiation therapy, a common treatment regime for cancer, can cause severe damage to radiosensitive organs, including the bone marrow, the gastrointestinal (GI) tract, and the lung. Toxic effects of radiation on the gastrointestinal system cause symptoms such as nausea, vomiting, diarrhea, electrolyte imbalance, and dehydration. Radiation can also cause pulmonary injury, leading to pulmonary pneumonitis and fibrosis.

Radiation toxicity not only causes devastating effects on the quality of patient life, but can sometimes even be more life-threatening than the primary tumor or cancer. Therefore, it is important to monitor the severity of radiation toxicity in patients during the course of radiation therapy.

Currently, there is no biomarker that indicates whether a person develops radiation toxicity. There is also no biomarker that can accurately determine the radiation dose absorbed by a person having radiation exposure.

The anoctamin (ANO, also known as TMEM16) protein family, which consists of 10 members (ANO 1-10) in mammals, is a family of transmembrane proteins having $Ca^{2+}$-activated $Cl^-$ activity. ANO proteins play a role in various diseases including cancer. It has been reported that ANO1 (also known as TMEM16a) is upregulated in gastrointestinal stromal tumor, as well as in oral and head and neck squamous cell carcinoma. It has been also reported that ANO5 (also known as TMEM16e) mutations in humans cause gnathodiaphyseal dysplasia. In addition, it has been reported that ANO7 (also known as TMEM16g) is selectively expressed in normal and cancerous prostates and regulates cell-cell aggregation.

Anoctamin proteins have not previously been reported as being associated with radiation toxicity.

BRIEF SUMMARY

In one embodiment, the present invention pertains to the use of anoctamin as an early biomarker for radiation biodosimetry. In a specific embodiment, the present invention relates to the use of anoctamin as a biomarker for diagnosing the presence of radiation toxicity in a subject who has been exposed to ionizing radiation.

In another embodiment, the present invention relates to the use of anoctamin as a biomarker for determining the absorbed radiation dose in a subject who has been exposed to a known or unknown dose of ionizing radiation.

Advantageously, the diagnostic and prognostic assays of the present invention are rapid, sensitive, and non-invasive. The present invention can be useful in civilian and military industries.

In one embodiment, the present invention provides a method for determining radiation dose absorbed by a subject who has been, or is suspected of having been, exposed to ionizing radiation, wherein the method comprises:

(a) providing a biological sample from a subject who has been, or is suspected of having been, exposed to ionizing radiation;

(b) determining anoctamin expression level in the subject's biological sample; and (c) determining the radiation dose absorbed by the subject based on the level of expression determined in step (b).

In another embodiment, the present invention provides a method of determining whether a subject has radiation toxicity, wherein the method comprises:

(a) providing a biological sample from a subject who has been, or is suspected of having been, exposed to ionizing radiation;

(b) determining anoctamin expression level in the subject's biological sample; and (c) comparing the expression level determined in step (b) to a level of anoctamin expression in a normal control;

wherein an increased expression of anoctamin in the subject's biological sample with respect to the control indicates that the subject has radiation toxicity.

In one embodiment, the absorbed radiation dose and/or the presence of radiation toxicity is determined based on the ANO1 expression level in a biological sample. In specific embodiments, the biological sample is a blood sample (such as whole blood, plasma, and serum).

In another embodiment, expression level of anoctamin can be used as a secondary endpoint to determine mechanisms of action and/or pharmacodynamic (PD) effects of an agent for reducing radiation toxicity.

BRIEF DESCRIPTION OF SEQUENCES

Figure 1A:
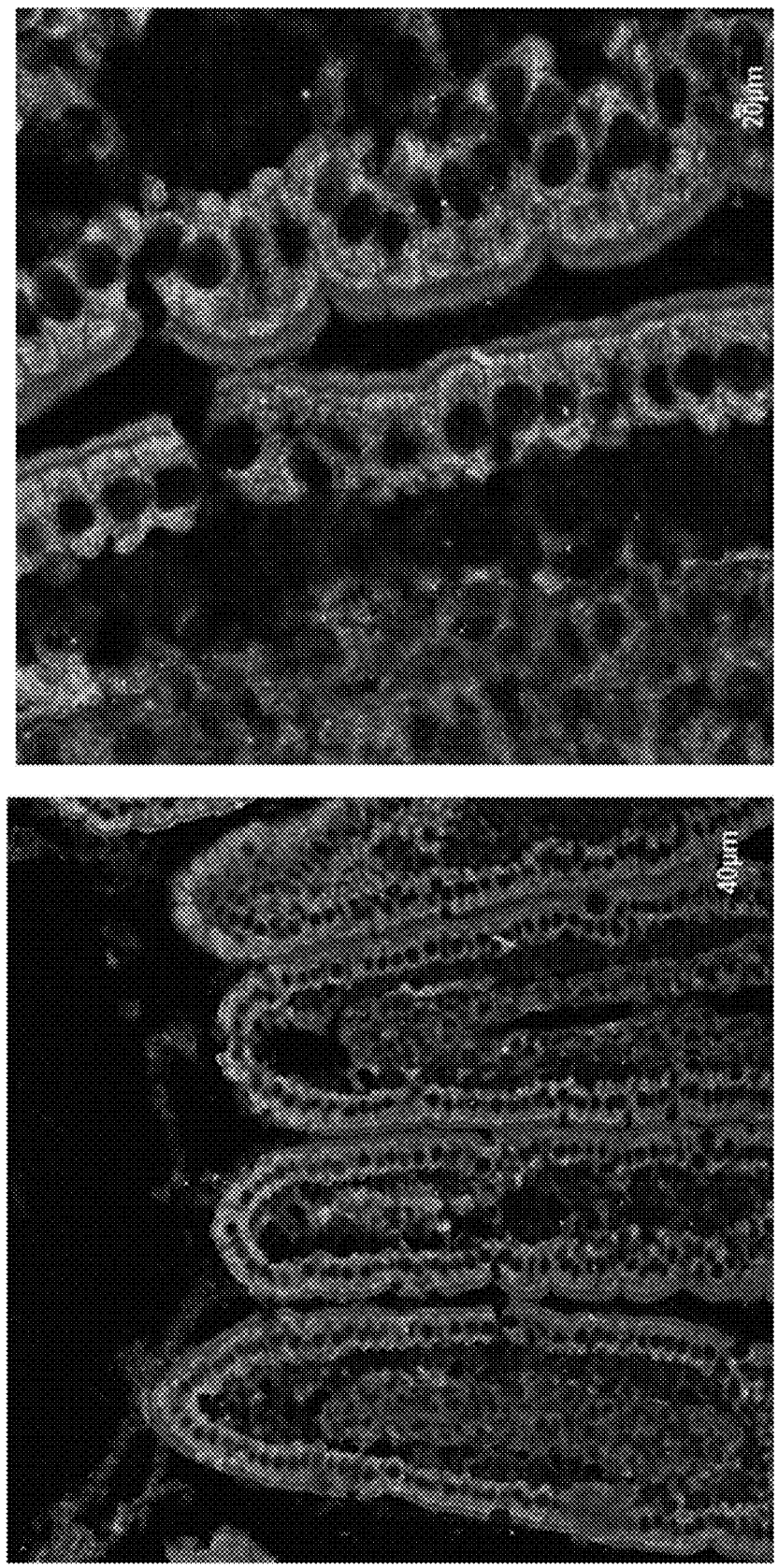
FIG. 1 (A-C) shows the anoctamin 1 protein in normal, non-irradiated mouse cells.

SEQ ID NO:1 is the amino acid sequence of a human anoctamin 1 protein (GenBank Accession No. NP_060513).
SEQ ID NO:2 is the nucleic acid sequence of a human anoctamin 1 mNRA transcript (GenBank Accession No. NM_018043).

DETAILED DISCLOSURE

In one embodiment, the present invention relates to the use of anoctamin as a biomarker for diagnosing the presence of radiation toxicity, specifically, radiation-induced acute gastrointestinal toxicity, in a subject who has been exposed to radiation (such as ionizing radiation). In another embodiment, the present invention relates to the use of anoctamin as a biomarker for determining the absorbed radiation dose in a subject who has been exposed to a known or unknown dose of radiation (such as ionizing radiation).

In another embodiment, the present invention relates to the use of anoctamin as a biomarker for determining effectiveness of a therapy for reducing radiation toxicity. In one embodiment, the expression level of anoctamin can be used as a secondary endpoint to determine mechanisms of action and/or pharmacodynamic (PD) effects of an agent for reducing radiation toxicity.

After irradiation, glucose transport is partially or completely down-regulated in a dose-dependent manner. As a result, oral glucose intake after irradiation would activate calcium-activated electrogenic chloride secretion, thereby resulting in secretory diarrhea. Western blot analysis of the small intestinal mucosa of mice exposed to irradiation shows increased anoctamin-1 expression even on day 6 post-irradiation. Anoctamin-1 expression level is also increased in the membrane of red blood cells (RBCs) after irradiation.

In one embodiment, the present invention provides a method for determining radiation dose absorbed by a subject who has been, or is suspected of having been, exposed to ionizing radiation, wherein the method comprises:
(a) providing a biological sample from a subject who has been, or is suspected of having been, exposed to radiation (such as ionizing radiation);
(b) determining expression level of an anoctamin (such as anoctamin 1) in the subject's biological sample; and
(c) determining the radiation dose absorbed by the subject based on the level of expression determined in step (b).

In another embodiment, the present invention provides a method of determining whether or not a subject has radiation toxicity, wherein the method comprises:
(a) providing a biological sample from a subject who has been, or is suspected of having been, exposed to radiation (such as ionizing radiation);
(b) determining expression level of an anoctamin (such as anoctamin 1) in the subject's biological sample; and
(c) comparing the expression level determined in step (b) to a level of an anoctamin (such as anoctamin 1) expression in a normal control;
wherein an increased expression of an anoctamin (such as anoctamin 1) in the subject's biological sample with respect to the control indicates that the subject has radiation toxicity.

In one embodiment, an increased expression of an anoctamin (such as anoctamin 1) in the subject's biological sample with respect to the control indicates that the subject has radiation-induced acute gastrointestinal toxicity.

In a further embodiment, the present invention provides a method of determining whether a subject has developed radiation toxicity during the course of radiation therapy, wherein the method comprises:
(a) providing a biological sample from a subject who has been prescribed radiation therapy at a predetermined dose;
(b) before radiation therapy, determining expression level of an anoctamin (such as anoctamin 1) in a biological sample of the subject;
(c) providing radiation therapy to the subject at the predetermined dose;
(d) determining expression level of an anoctamin (such as anoctamin 1) in the subject's biological sample after the subject has been exposed to radiation at the predetermined dose;
(e) comparing the expression level determined in step (d) to the anoctamin (such as anoctamin 1) expression level determined in step (b); and
(d) if the level of anoctamin (such as anoctamin 1) expression determined in (d) is at least 105%, 110%, 115%, 120%, 125%, 130%, 135%, 140%, 150%, 160%, 170%, 180%, 190%, 200%, 250%, 300%, 400%, or 500% of the anoctamin (such as anoctamin 1) expression level determined in step (b), then the subject has radiation toxicity.

In certain embodiments, the present invention can be used to determine the absorbed radiation dose and/or determine the presence of radiation toxicity 1, 2, 3, 4, 5, 6, 7, 8, 9, 10, 11, 12, 13, or 14 days after the subject has received, or is suspected of receiving, irradiation.

In certain embodiments, anoctamin (e.g., ANO 1) expression level is determined using a biological sample obtained no more than 1, 2, 3, 4, 5, 6, 7, 8, 9, 10, 11, 12, 13, or 14 days after the subject has received, or is suspected of receiving, ionizing radiation.

In certain embodiments, anoctamin (e.g., ANO 1) expression level is determined using a biological sample obtained no more than 1, 2, 3, 4, 5, 6, 7, 8, 9, 10, 11, 12, 13, or 14 days after the subject has received, or is suspected of receiving, radiation at a dose of at least 0.5 Gy or higher (including, but not limited to, at least 2, 3, 4, 5, 6, 7, 8, 9, 10, 15, 20, 25, 30, 35, 40, 45, 50, 55, 60, 65, 70, 80, 85, and 90 Gy).

In one embodiment, the absorbed radiation dose and/or the presence of radiation toxicity is determined based on the ANO1 expression level in a biological sample. In one embodiment, the biological sample is a blood sample (such as whole blood, plasma, and serum). In one embodiment, the level of an anoctamin (e.g., ANO 1) in the membranes of RBCs of a subject is determined.

In a further embodiment, the anoctamin expression level in a subject is determined at multiple time points to determine whether the subject has radiation toxicity, to monitor the severity of radiation toxicity, and/or to determine the treatment effects of a therapeutic regime for reducing radiation toxicity.

The term "subject," as used herein, describes an organism, including mammals such as primates. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters. In one embodiment, the subject is a human.

In one embodiment, the subject has been exposed to radiation during the course of radiation therapy for tumor or cancer. In another embodiment, the subject has been, or is suspected of having been, exposed to ionizing radiation by accident.

In certain embodiments, the subject has been exposed to radiation (such as via prescription during ionizing radiation therapy) or is suspected of having been exposed to radiation (such as by accidental exposure to ionizing radiation) at a dose of at least 0.5, 1, 2, 3, 4, 5, 6, 7, 8, 9, 10, 15, 20, 25, 30, 35, 40, 45, 50, 55, 60, 65, 70, 80, 85, or 90 Gy. In certain embodiments, the subject has been exposed to radiation (such as via prescription during ionizing radiation therapy) or is suspected of having been exposed to radiation (such as by accidental exposure to ionizing radiation) at a dose of at least 0.1, 0.3, 0.5, 0.7, 0.9, 1.0, 1.1, 1.2, 1.3, 1.4, 1.5, 1.6, 1.7, 1.8, 1.9, 2.0, 2.1, 2.2, 2.3, 2.4, 2.5, 2.7, 3.0, 3.2, 3.5, or 4.0 Gy in one day.

In a further embodiment, the present invention provides a method of providing a toxicity-monitored radiation therapeutic regime, wherein the method comprises:

(a) providing a biological sample from a subject who has been exposed to radiation therapy at a predetermined dose;

(b) determining anoctamin (e.g., ANO 1) expression level in the subject's biological sample after the subject has been exposed to radiation at the predetermined dose;

(c) comparing the expression level determined in step (b) to a level of anoctamin (e.g., ANO 1) expression in a normal control;

(d) if the level of anoctamin (e.g., ANO 1) expression determined in (b) is greater than control, then prescribing additional radiation at a dose lower than the predetermined dose, discontinuing radiation therapy for at least 1 day or any days longer than 1 day (including, but not limited to, at least 2 days, 3 days, 4 days, 5 days, 10 days, 15 days, 30 days, 60 days, 90 days, and 180 days), or prescribing a therapy that reduces radiation-induced toxicity (such as radiation-induced acute gastrointestinal toxicity); and if the level of anoctamin (e.g., ANO 1) expression determined in (b) is no greater than the control, then continuing radiation therapy at a dose identical to, or higher than, the predetermined dose.

In a further embodiment, the present invention provides a method of providing a toxicity-monitored radiation therapeutic regime, wherein the method comprises:

(a) providing a biological sample from a subject who has been prescribed radiation therapy at a predetermined dose;

(b) before radiation therapy, determining anoctamin (e.g., ANO 1) expression level in a biological sample of the subject;

(c) providing radiation therapy to the subject at the predetermined dose;

(d) determining anoctamin (e.g., ANO 1) expression level in the subject's biological sample after the subject has been exposed to radiation at the predetermined dose;

(e) comparing the expression level determined in step (d) to the anoctamin (e.g., ANO 1) expression level determined in step (b);

(f) if the level of anoctamin (e.g., ANO 1) expression determined in (d) is at least 105%, 110%, 115%, 120%, 125%, 130%, 135%, 140%, 150%, 160%, 170%, 180%, 190%, 200%, 250%, 300%, 400%, or 500% of the anoctamin (e.g., ANO 1) expression level determined in step (b), then prescribing a second radiation dose lower than the predetermined dose, discontinuing radiation therapy for at least 1 day or any days longer than 1 day (including, but not limited to, at least 2 days, 3 days, 4 days, 5 days, 10 days, 15 days, 30 days, 60 days, 90 days, and 180 days), or prescribing a therapy that reduces radiation-induced toxicity (such as radiation-induced acute gastrointestinal toxicity); and if the level of anoctamin (e.g., ANO 1) expression determined in (d) is no greater than 105%, 110%, 115%, 120%, 125%, 130%, 135%, 140%, 150%, 160%, 170%, 180%, 190%, 200%, 250%, 300%, 400%, or 500% of the anoctamin (e.g., ANO 1) expression level determined in step (b), then continuing the prescribed radiation dose.

In certain embodiments, in the course of providing a toxicity-monitored radiation therapeutic regime, anoctamin (e.g., ANO 1) expression level is determined 1, 2, 3, 4, 5, 6, 7, 8, 9, 10, 11, 12, 13, or 14 days after the subject has received the predetermined radiation dose. The anoctamin (e.g., ANO 1) expression level can be determined at multiple time points over time. In certain embodiments, therapies that reduce radiation-induced toxicity (such as radiation-induced acute gastrointestinal toxicity) include, but are not limited to, oral rehydration compositions, and compositions disclosed in PCT/US2011/053265, which is hereby incorporated by reference in its entirety.

The term "biological sample," as used herein, includes, but is not limited to, a sample containing tissues, cells, and/or biological fluids isolated from a subject. Examples of biological samples include but, are not limited to, tissues, cells, biopsies, blood, lymph, serum, plasma, urine, saliva, and tears. In one embodiment, the biological sample contains red blood cells.

In one embodiment, the absorbed radiation dose and/or the presence of radiation toxicity is determined based on expression level(s) of one or more anoctamins selected from the group consisting of anoctamin 1, anoctamin 2, anoctamin 3, anoctamin 4, anoctamin 5, anoctamin 6, anoctamin 7, anoctamin 8, anoctamin 9, and anoctamin 10.

The level of anoctamin expression can be determined based on mRNA levels or protein levels. Determination of anoctamin expression can be made qualitatively, semi-quantitatively, or quantitatively. Sequences of anoctamin proteins and mRNAs of a variety of mammalian species are publicly available and can be obtained from, for example, the GenBank database. In one embodiment, the human anoctamin 1 protein has the amino acid sequence of SEQ ID NO:1 (GenBank Accession No. NP_060513). In another embodiment, the human anoctamin 1 mNRA transcript has the nucleic acid sequence of SEQ ID NO:2 (GenBank Accession No. NM_018043). One of ordinary skill in the art, having the benefit of the present disclosures, can easily use anoctamin protein and nucleic acid sequences of a mammalian species of interest to practice the present invention.

In one embodiment, the control level of anoctamin expression is determined by measuring anoctamin expression in a healthy population that has not been exposed to radiation (such as ionizing radiation) and/or does not have acute or long term side effects caused by irradiation.

Methods for determining anoctamin expression level are well known in the art, including but not limited to, Western blot, enzyme-linked immunosorbent assay (ELISA), immunoprecipitation, polymerase chain reaction (PCR) methods including reverse transcription polymerase chain reaction (RT-PCR), nucleic acid hybridization, and any combination thereof. In a preferred embodiment, the anoctamin expression level is determined using ELISA.

A contacting step in the assay (method) of the invention can involve contacting, combining, or mixing the biological sample and a solid support, such as a reaction vessel, microbeads, microvessel, tube, microtube, well, multi-well plate, or other solid support.

An antibody that specifically recognizes, or specifically binds to, anoctamin proteins (e.g., ANO1) can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment; and human or humanized immunoglobulin molecules or fragments thereof.

"Specific binding" or "specificity" refers to the ability of a protein to detectably bind an epitope presented on a protein or polypeptide molecule of interest, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific target molecule versus nonspecific binding to other irrelevant molecules.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the present invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

In one embodiment, the level of anoctamin (e.g., ANO1) protein expression is determined by contacting the biological sample with an antibody that specifically recognizes, or specifically binds to, an anoctamin protein (e.g., ANO1); and detecting the complex formed between the antibody and the anoctamin (e.g., ANO1) protein.

The level of anoctamin (e.g., ANO1) expression can be determined based on anoctamin (e.g., ANO1) mRNA level. In one embodiment, the anoctamin mRNA level can be determined by a method comprising contacting the biological sample with a polynucleotide probe that comprises a nucleic acid sequence that specifically binds to, or hybridizes under stringent conditions with, an anoctamin (e.g., ANO1) mRNA; and detecting the complex formed between the polynucleotide probe and the anoctamin (e.g., ANO1) mRNA.

As used herein, "stringent" conditions for hybridization refers to conditions wherein hybridization is typically carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm = 81.5 C + 16.6 \text{ Log } [Na+] + 0.41(\% G+C) - 0.61(\% \text{ formamide}) - 600/\text{length of duplex in base pairs}.$$

Washes are carried out as follows:
(1) Twice at room temperature for 15 minutes in 1×SSPE, 0.1% SDS (low stringency wash).
(2) Once at Tm−20 C for 15 minutes in 0.2×SSPE, 0.1% SDS (moderate stringency wash).

In one embodiment, the anoctamin mRNA level can be determined by polymerase chain reaction methods. Polymerase chain reaction (PCR) is a process for amplifying one or more target nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. The skilled artisan, to detect the presence of a desired sequence (U.S. Pat. No. 4,683,195), routinely uses polymerase chain reaction.

A specific example of PCR that is routinely performed by the skilled artisan to detect desired sequences is reverse transcript PCR (RT-PCR; Saiki et al., *Science*, 1985, 230: 1350; Scharf et al., *Science*, 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

Samples and/or anoctamin (e.g., ANO1)-specific binding agents may be arrayed on a solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or "physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or 1536-well plates (or trays). Optionally, anoctamin (e.g., ANO1)-specific binding agents may be immobilized on the solid support.

In another embodiment, the present invention provides a method for screening for a therapeutic agent that reduces radiation toxicity, wherein the method comprises:

(a) providing a population of cells that have been exposed to radiation (such as ionizing radiation) and have an increased expression of anoctamin (e.g., ANO1), and optionally, determining a first level of anoctamin (e.g., ANO1) expression in the population of cells exposed to radiation (such as ionizing radiation);

(b) contacting the population of cells with a candidate therapeutic agent for reducing radiation toxicity;

(c) after step (b), determining anoctamin (e.g., ANO1) expression level in the population of cells contacted with the candidate therapeutic agent; and (d) selecting the candidate agent that reduces the level of anoctamin (e.g., ANO1) expression as the therapeutic agent that reduces radiation toxicity.

In another embodiment, the present invention provides a method for identifying an agent that increases radiation toxicity, wherein the method comprises:

(a) providing a population of cells that have been exposed to radiation (such as ionizing radiation) and have an increased expression of anoctamin (e.g., ANO1), and optionally, determining a first level of anoctamin (e.g., ANO1) expression in the population of cells exposed to radiation (such as ionizing radiation);

(b) contacting the population of cells with a candidate agent;

(c) after step (b), determining anoctamin (e.g., ANO1) expression level in the population of cells contacted with the candidate agent; and (d) identifying the candidate agent that increases the level of anoctamin (e.g., ANO1) expression, when compared to the first level of anoctamin (e.g., ANO1) expression, as an agent that increases radiation toxicity.

In a further embodiment of the screening method, the candidate agent is contacted with a population of cells of a subject who has been exposed to radiation (such as ionizing radiation).

Kits

The present invention provides kits comprising the required elements for detecting anoctamins (e.g., ANO1).

In one embodiment, the present invention provides a kit for determining whether the subject has radiation toxicity, for determining the absorbed radiation dose, for monitoring the severity of radiation toxicity, and/or for determining the treatment effects of a therapeutic regime for reducing radiation toxicity.

In certain specific embodiments, the kit comprises an application zone for receiving a biological sample (such as a blood sample); a labeling zone containing a binding agent that binds to an anoctamin (e.g., ANO 1) protein or mRNA in the sample; and a detection zone where anoctamin (e.g., ANO 1)-bound binding agent is retained to give a signal, wherein the signal given for a sample of a subject with an anoctamin (e.g., ANO 1) level greater than a control level is different from the signal given for a sample of a subject with an anoctamin (e.g., ANO 1) level lower than a control level.

In one embodiment, the kit comprises an anoctamin-binding agent including, an antibody that specifically recognizes, or specifically binds to, an anoctamin protein (e.g., ANO1); a polynucleotide probe that comprises a nucleic acid sequence that specifically binds to, or hybridizes under highly stringent condition to, an anoctamin (e.g., ANO1) mRNA; and a primer set that amplifies an anoctamin (e.g., ANO1) mRNA.

Preferably, the kits comprise a container for collecting samples, such as blood samples, from a subject, and an agent for detecting the presence or the level of anoctamin (e.g., ANO1) in the sample. The agent may be any binding agent specific for anoctamin (e.g., ANO1), including, but not limited to, antibodies, aptamers, nucleic acid probes, and primers. The components of the kit can be packaged either in aqueous medium or in lyophilized form.

As indicated above, kits of the invention include reagents for use in the methods described herein, in one or more containers. The kits may include specific internal controls, and/or probes, buffers, and/or excipients, separately or in combination. Each reagent can be supplied in a solid form or liquid buffer that is suitable for inventory storage. Kits may also include means for obtaining a sample from a host organism or an environmental sample.

Kits of the invention can be provided in suitable packaging. As used herein, "packaging" refers to a solid matrix or material customarily used in a system and capable of holding within fixed limits one or more of the reagent components for use in a method of the present invention. Such materials include glass and plastic (e.g., polyethylene, polypropylene, and polycarbonate) bottles, vials, paper, plastic, and plastic-foil laminated envelopes and the like. Preferably, the solid matrix is a structure having a surface that can be derivatized to anchor an oligonucleotide probe, primer, molecular beacon, specific internal control, etc. Preferably, the solid matrix is a planar material such as the side of a microtiter well or the side of a dipstick. In certain embodiments, the kit includes a microtiter tray with two or more wells and with reagents including primers, probes, specific internal controls, and/or molecular beacons in the wells.

Kits of the invention may optionally include a set of instructions in printed or electronic (e.g., magnetic or optical disk) form, relating information regarding the components of the kits and/or how to make various determinations (e.g., anoctamin levels, comparison to control standards, etc.). The kit may also be commercialized as part of a larger package that includes instrumentation for measuring other biochemical components.

EXAMPLES

Following are examples that illustrate procedures and embodiments for practicing the invention. The examples should not be construed as limiting.

Example 1

Radiation Increases Anoctamin-1 Expression in Red Blood Cells

Anoctamin-1 expression level is increased in the membrane of red blood cells (RBCs) after irradiation. Briefly, RBC ghosts are prepared from mice that have been exposed to different radiation doses, and Western analysis is performed.

Figure 1B:
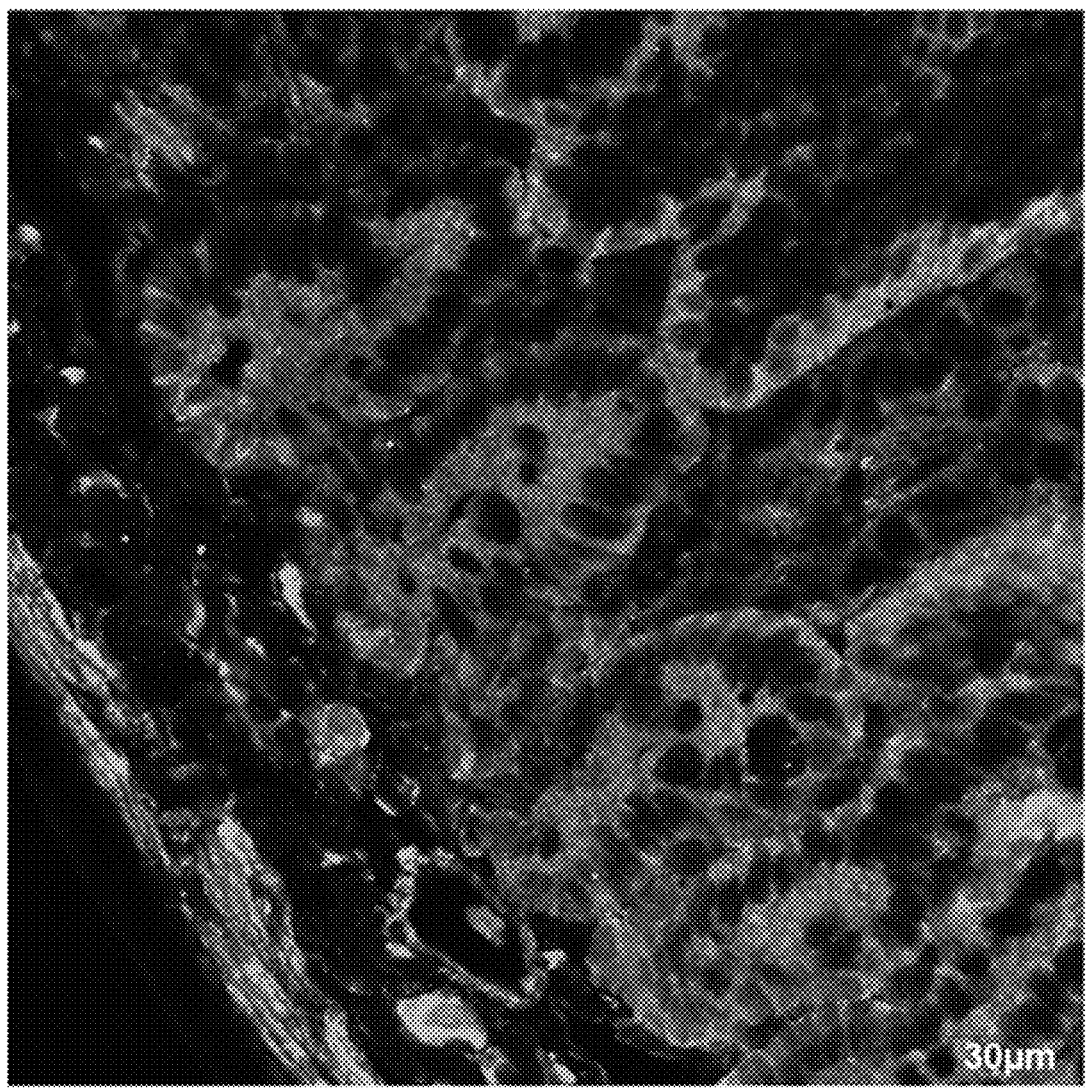
Figure 1C:
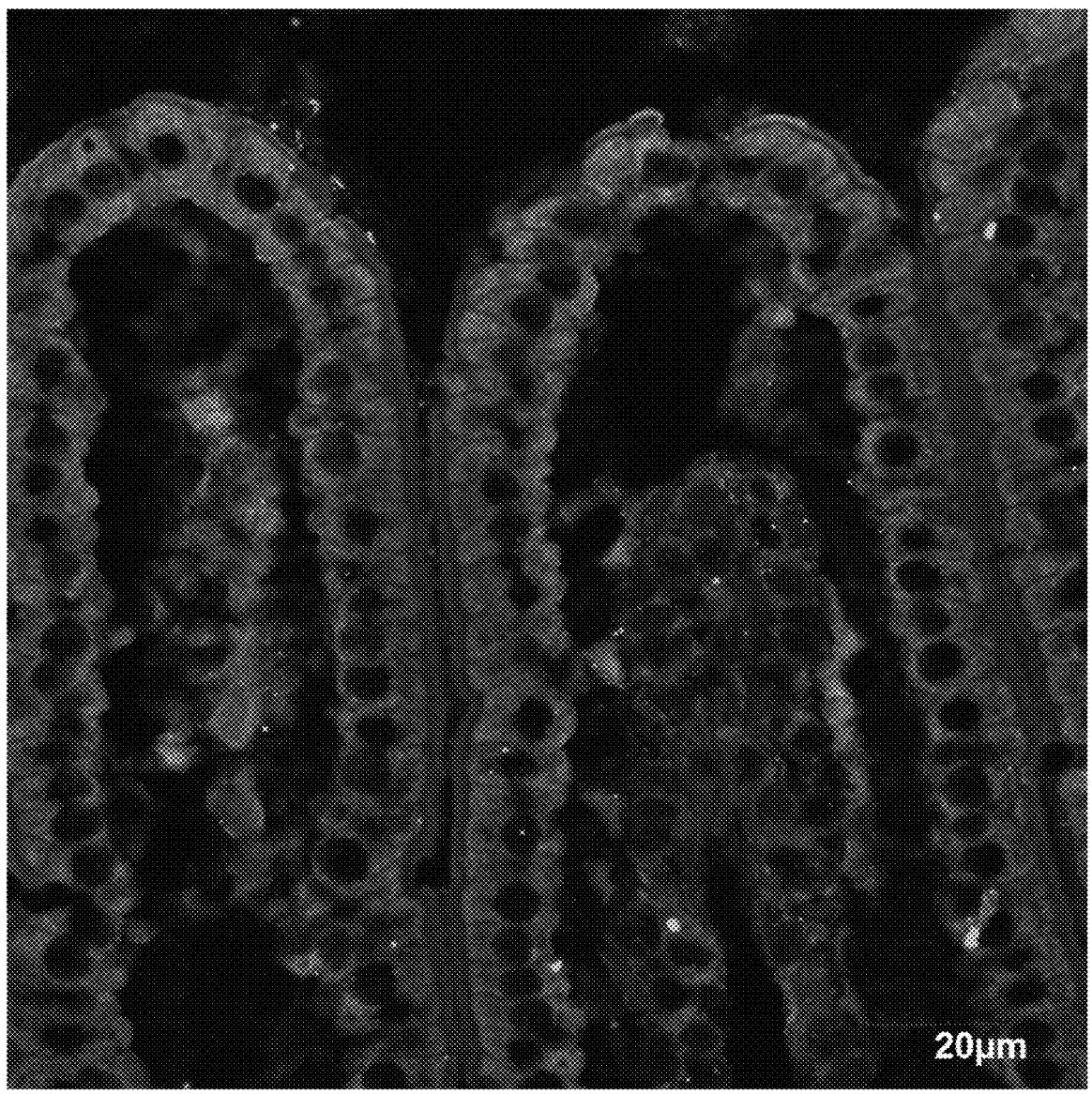
Figure 2A:
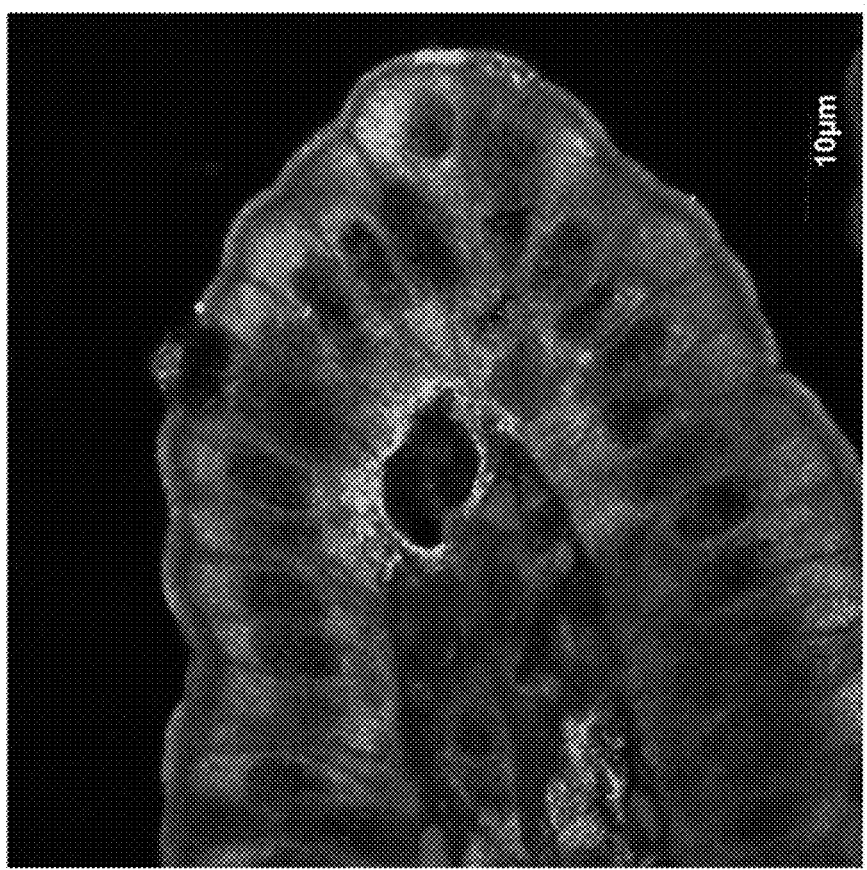
FIG. 2 (A-F) shows the anoctamin 1 protein in mouse cells 6 days after the mice received irradiation at 3 Gy, 5 Gy, and 7 Gy, respectively.
Figure 2A:
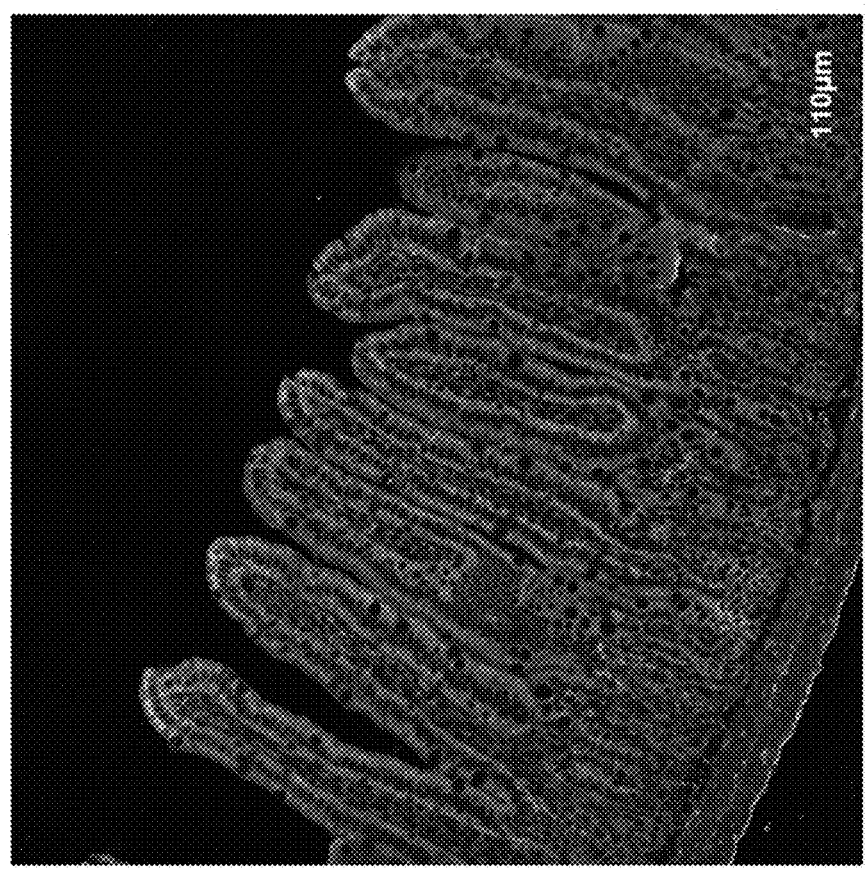
Figure 2B:
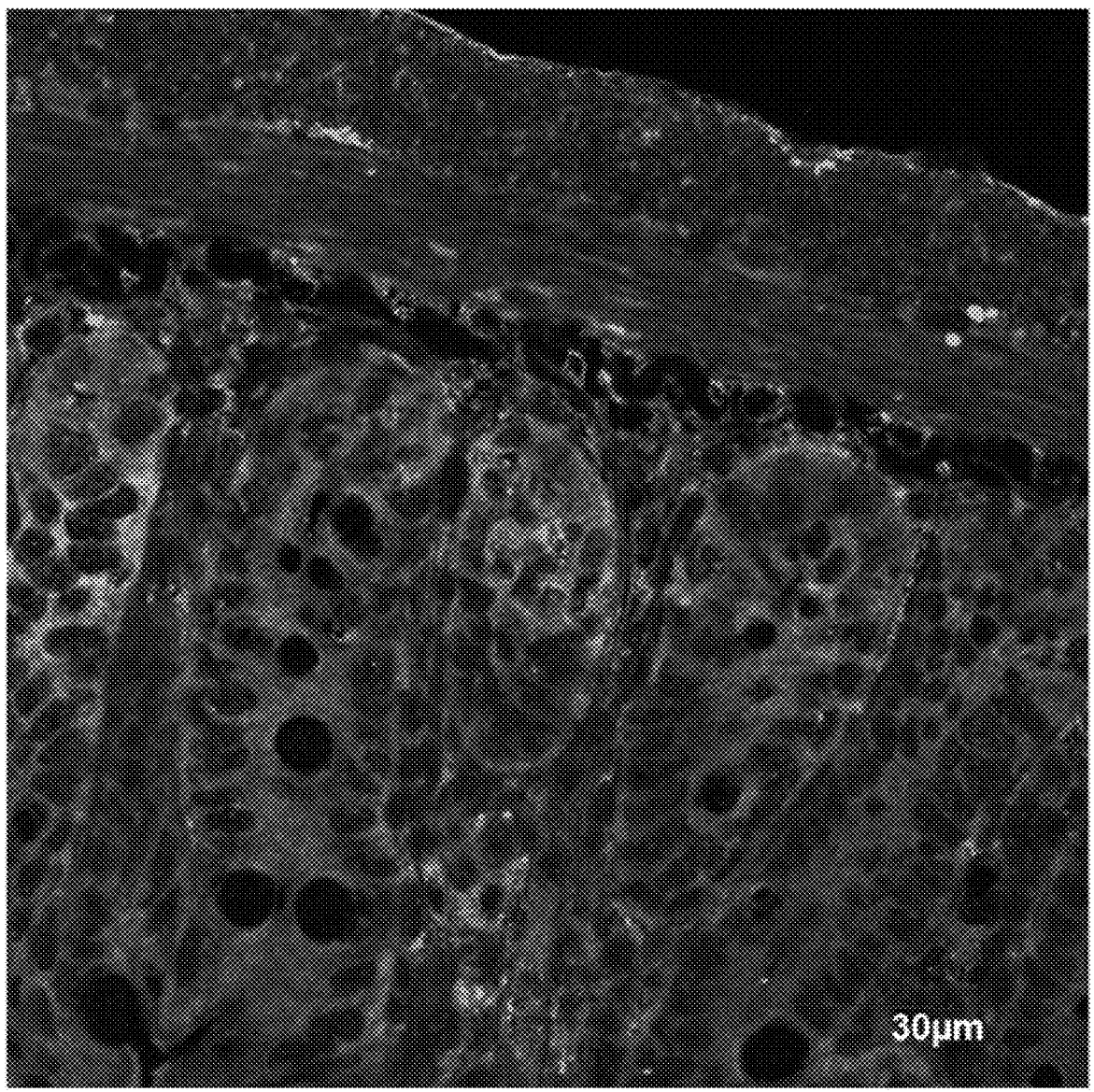
Figure 2C:
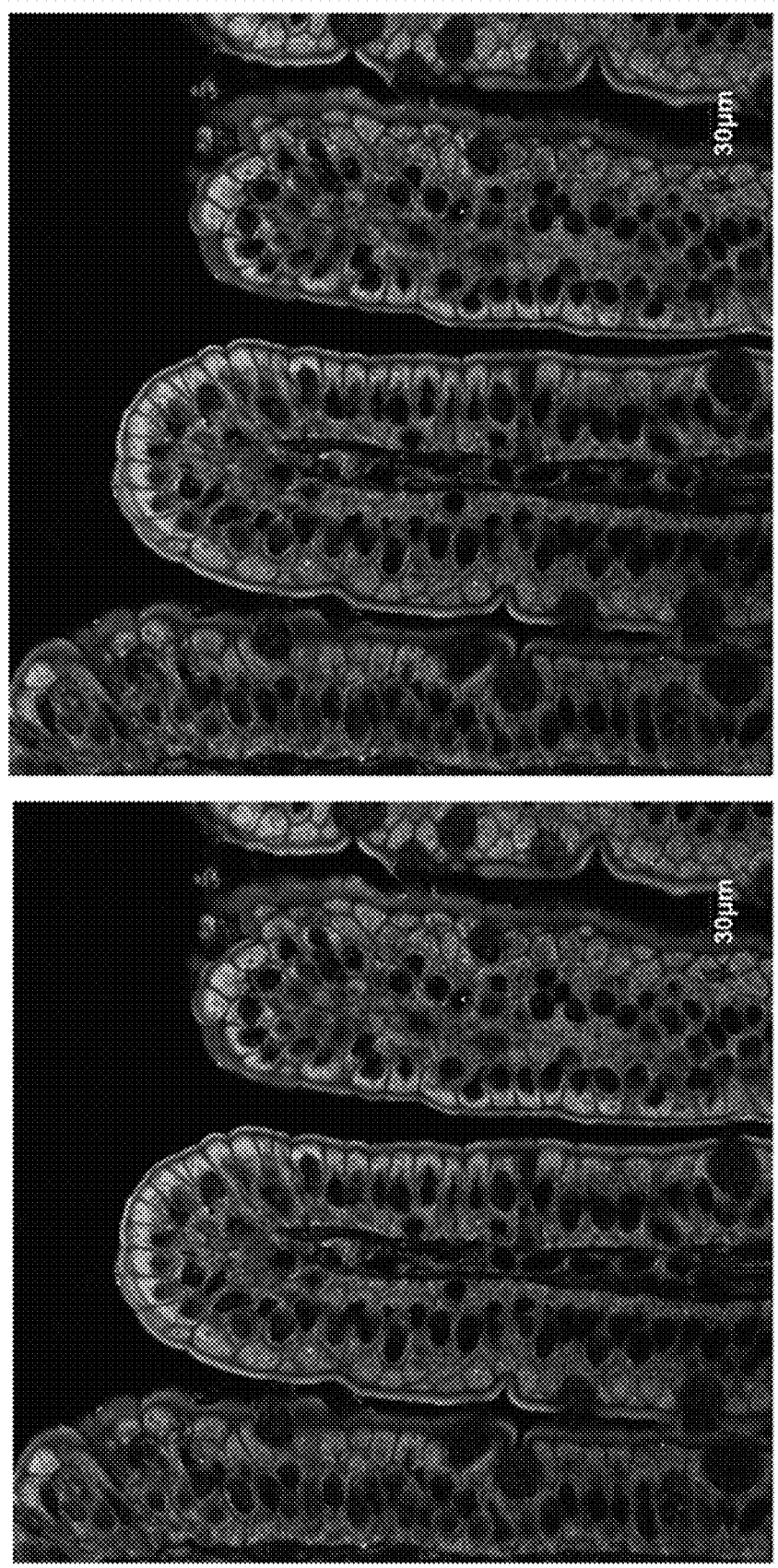
Figure 2D:
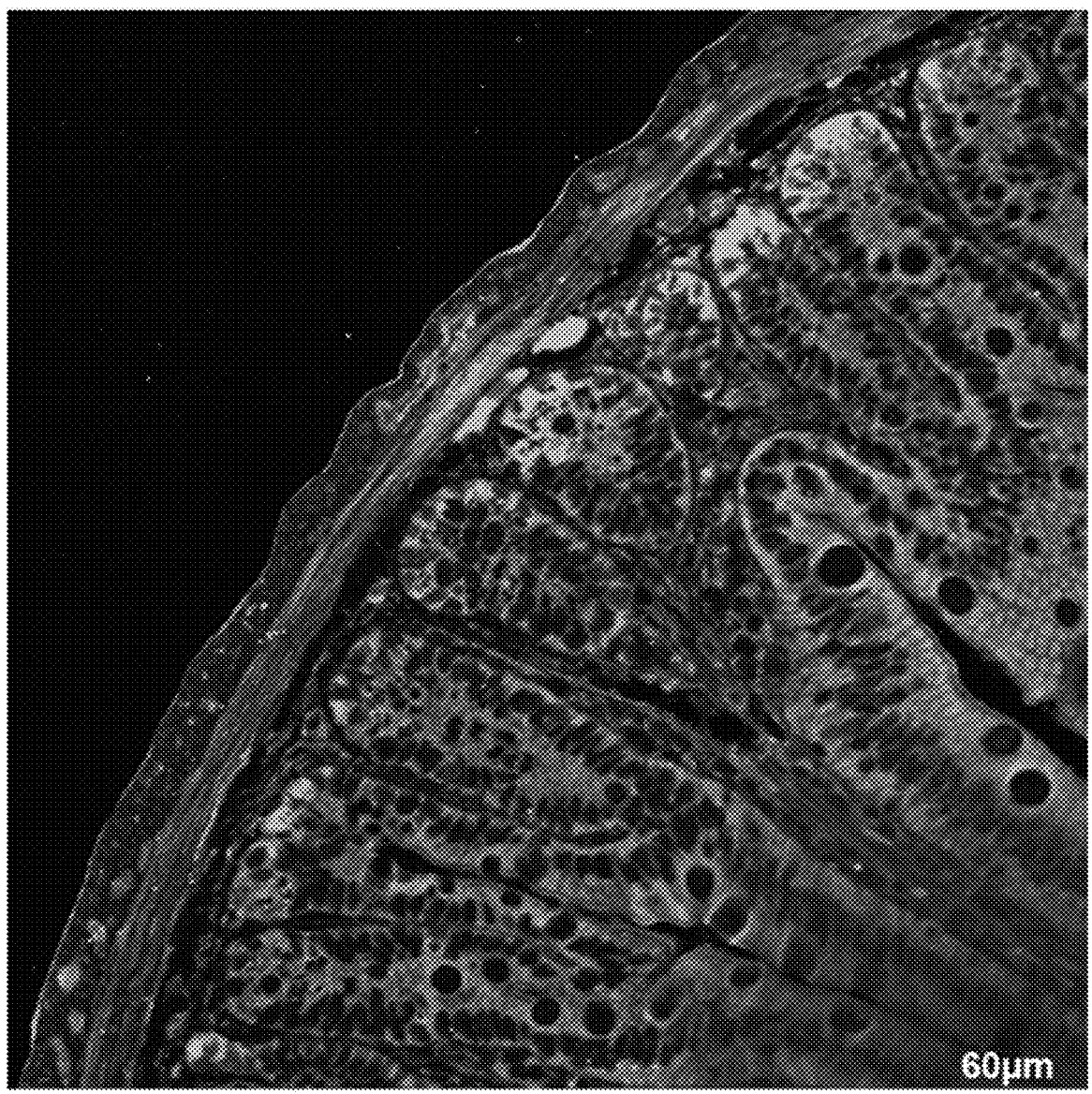
Figure 2E:
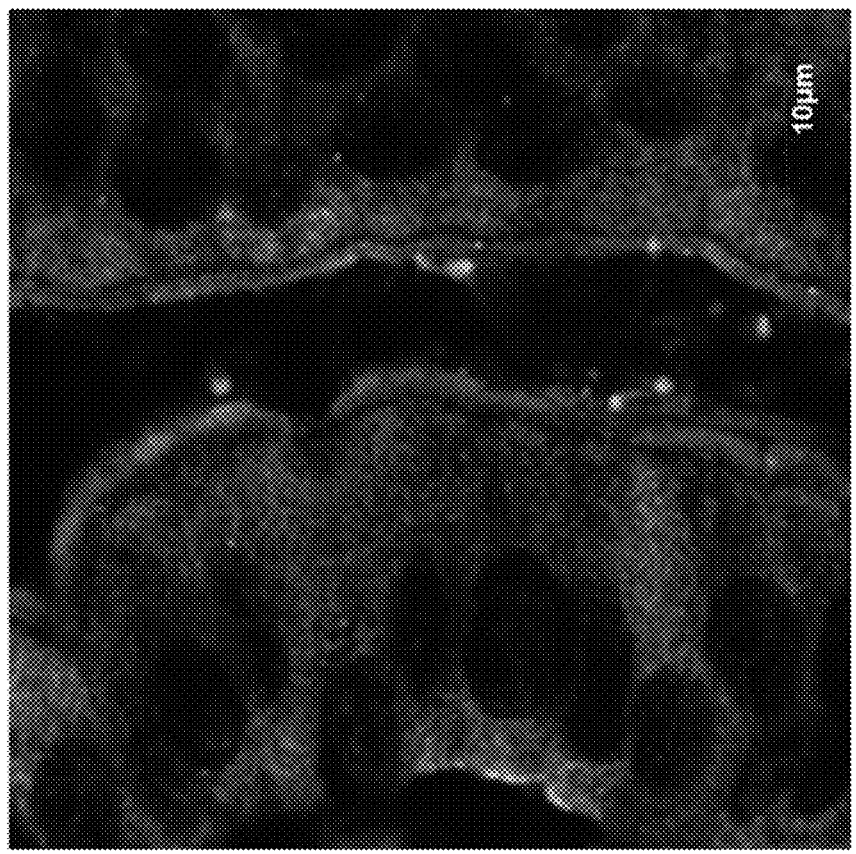
Figure 2E:
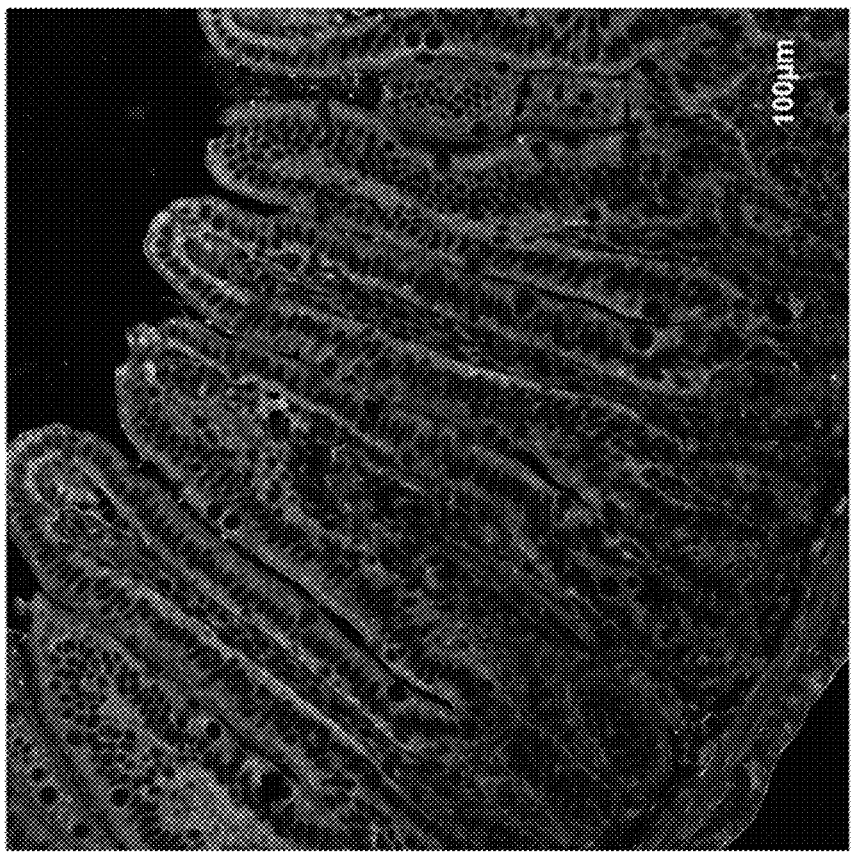
Figure 2F:
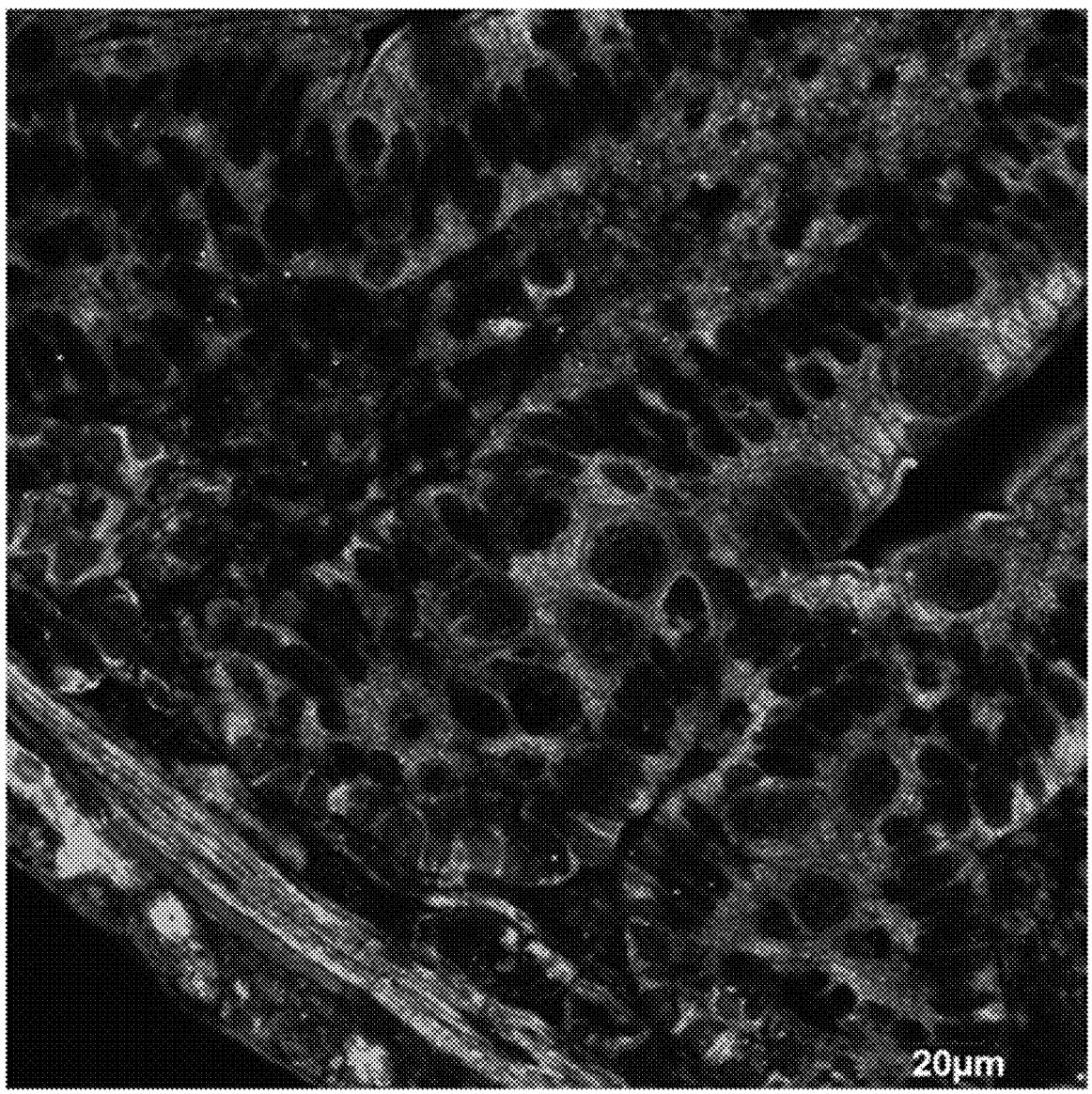
Figure 3:
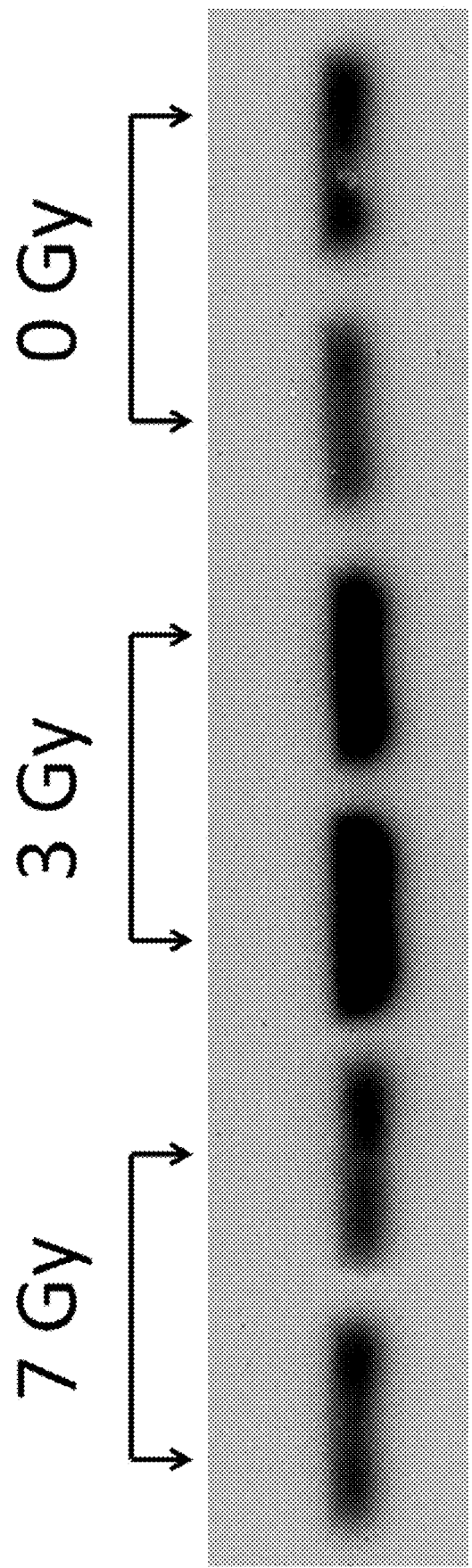
FIG. 3 shows anoctamin 1 protein expression level in mouse red blood cells 6 days after the mice received irradiation at 3 Gy, 5 Gy, and 7 Gy, respectively.
Figure 4:
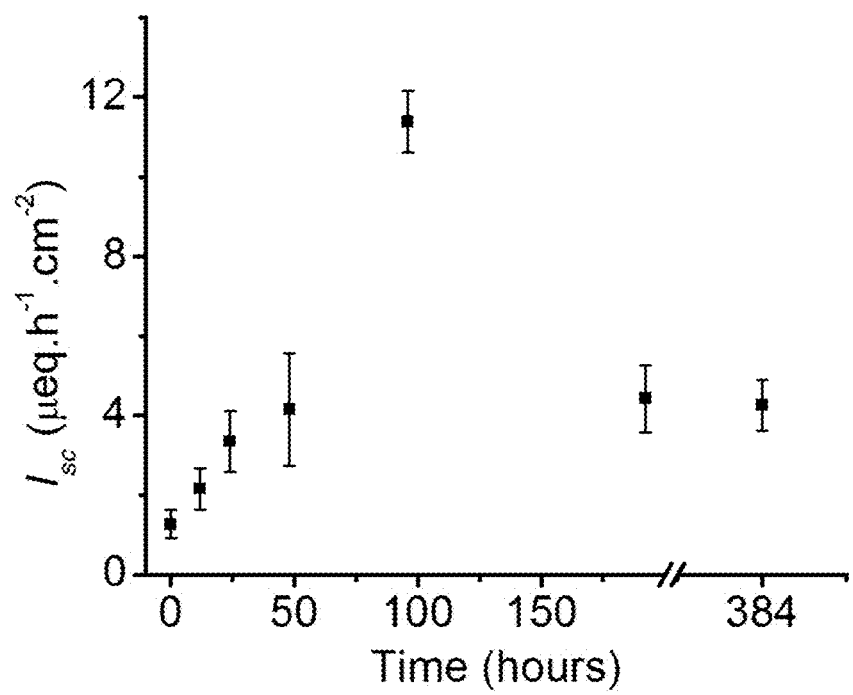
FIG. 4 shows changes in Isc with time since 3-Gy irradiation. The highest current was seen at 94 hours.
Figure 5:
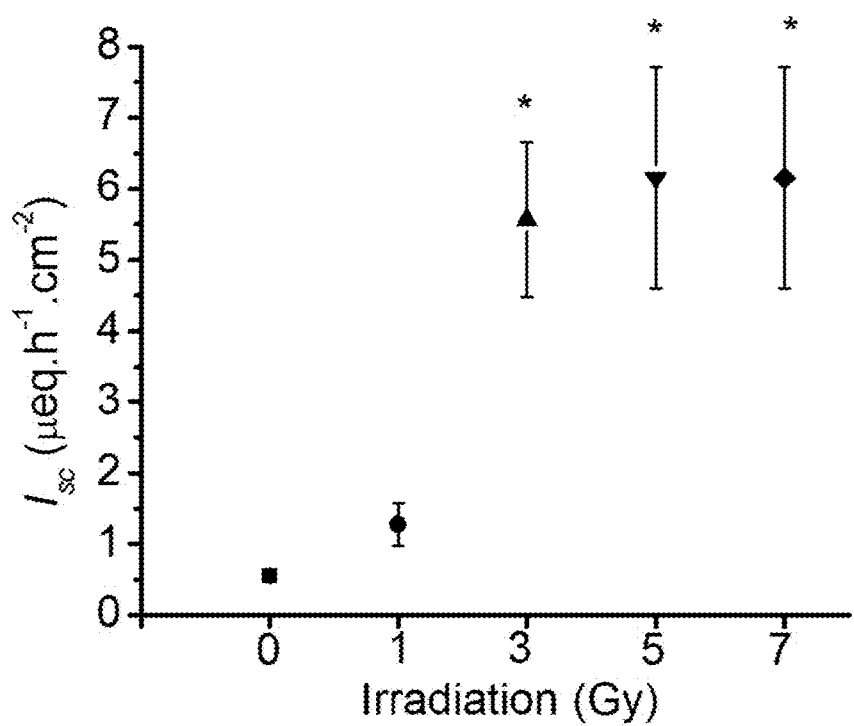
FIG. 5 shows changes in Isc with increasing dose of irradiation. A significant increase in Isc was seen in 3, 5, and 7 Gy compared to 0 Gy irradiated mice (P<0.01). All results are from n=6 tissues. Error bars represent standard error of mean (SEM).
Figure 6:
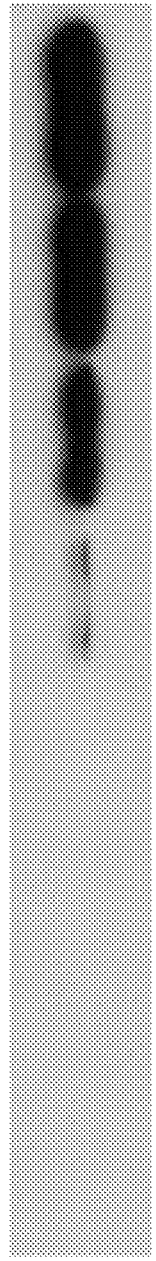
FIG. 6 shows the effect of irradiation dose on ANO1 protein levels. Ileal tissues were collected on day 6 following irradiation. Irradiation resulted in a dose-dependent increase in ANO1 protein levels.
Figure 7:
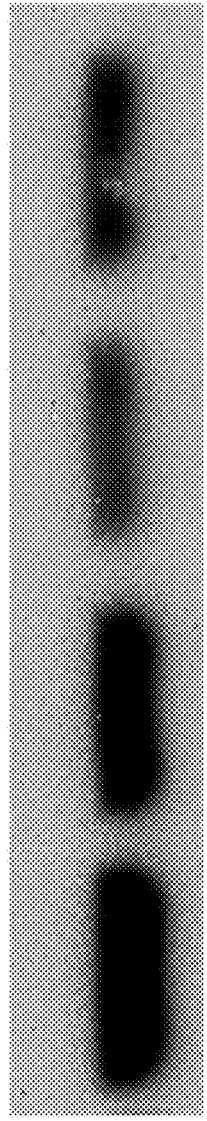
FIG. 7 shows the effect of irradiation dose on ANO1 protein level in red blood cell (RBC) ghost membrane on day 6 post-irradiation.
Figure 8:
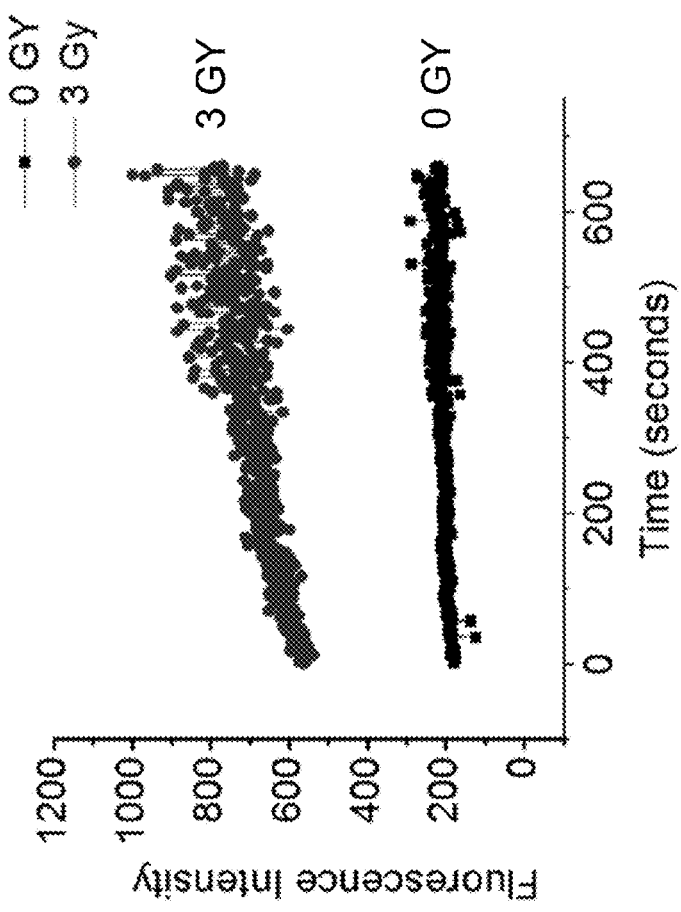
FIG. 8 shows the effect of irradiation on intracellular cAMP and intracellular calcium in mouse ileal epithelial cells. Radiation increases intracellular calcium and not cAMP. All measurements were made on day 6 following 3 Gy irradiation.
Figure 8:
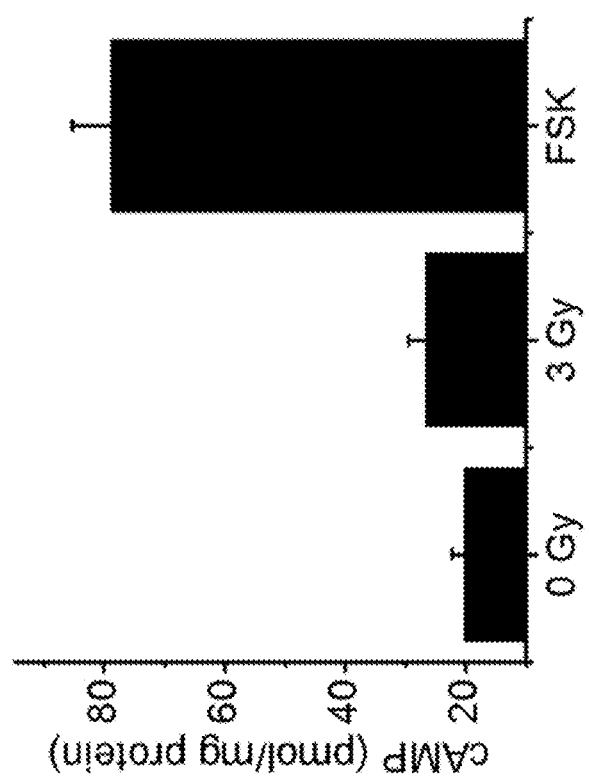
Figure 9:
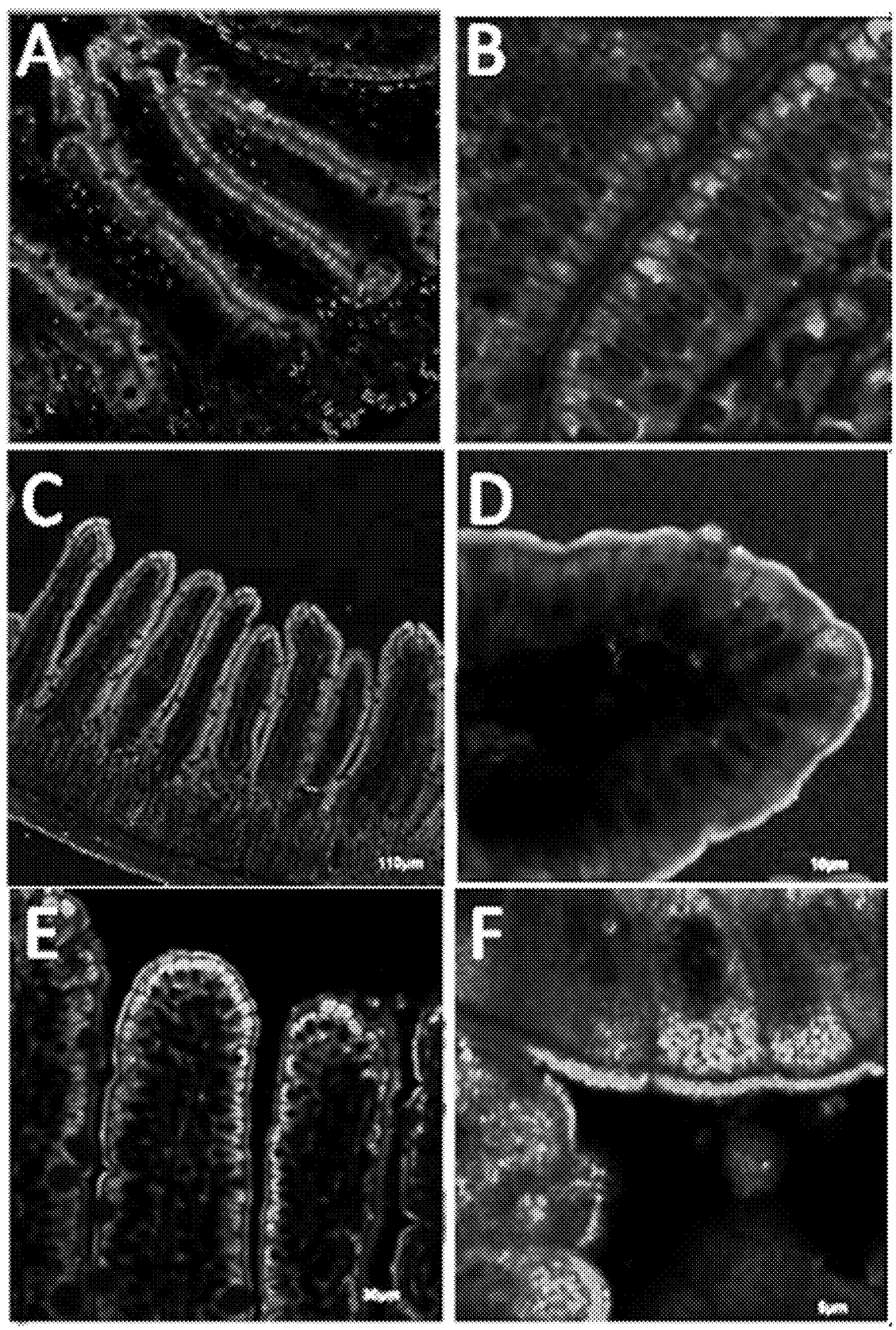
FIG. 9 shows immunohistochemistry sections for ANO1 expression in mouse small intestine. (A) and (B) show ANO1 expression in mouse ileum from 0 Gy irradiated mice. Most of the expression occurred in the villous epithelium with minimal expression in the brush border membrane region. (C) and (D) show ANO1 expression in mouse ileum from 3 Gy irradiated mice. ANO1 expression shows higher intensity in the brush border membrane region of villous cells. (E) and (F) show ANO1 expression in mouse ileum from 5 Gy irradiated mice. 5 Gy irradiated mice showed a higher degree of expression for the ANO1 chloride channel than tissues from 0 Gy and 3 Gy irradiated mice. The ANO1 protein was mostly expressed in the villous cell region with minimal expression in the crypt cell region.

FIG. 1 (A-C) shows the anoctamin 1 protein in normal, non-irradiated mouse cells. FIG. 2 (A-F) shows the anoctamin 1 protein in mouse cells 6 days after the mice received irradiation at 3 Gy, 5 Gy, and 7 Gy, respectively. FIG. 3 shows anoctamin 1 protein expression level in mouse red blood cells 6 days after the mice received irradiation at 3 Gy, 5 Gy, and 7 Gy, respectively.

As shown in FIG. 3, the Western analysis shows that there is a radiation dose-dependent increase in anoctamin-1 expression at a radiation dose of up to about 5 Gy, while there is a marginal decrease in anoctamin-1 expression at a radiation dose of about 7 Gy; it is postulated that 7 Gy causes increased cell death in the RBC cells used in the current experiments, thereby resulting in a marginal decrease in anoctamin-expression. Nevertheless, the anoctamin expression at a radiation dose of 7 Gy is higher than that of the non-irradiated mice.

Example 2

Ano1—a Biomarker for Radiation-Induced Acute Gastrointestinal Toxicity

Total body irradiation (TBI) results in a dose-dependent increase in gastric anion secretion. This Example shows that the expression level of ANO1 in RBC indicates acute gastrointestinal radiotoxicity.

Materials and Methods
Animal
Eight-week old NIH Swiss mice were used in this study.
Ussing Chamber
Murine ileal sections were used for transepithelial electrical current measurements after 0, 12, 24, 48, 96, 192, and 384 hours after TBI. Tissues were mounted in Ussing chambers, bathed in modified regular Ringer's solution, and gassed with 95% $O_2$ & 5% $CO_2$ to measure short circuit current (Isc), a measure of anion secretion. Basal readings were taken after 45 minutes, and the peak current was measured in chambers under different conditions (NSP4 and glucose+NSP4). The CaCC inhibitor niflumic acid was used to study the role of chloride secretion through CaCC.
RBC Ghosts
RBC ghosts were used, and changes in anoctamin 1 (ANO1) expression in RBC ghosts were determined.
Immunohistochemistry
Mice were irradiated with 0 Gy, 3 Gy, or 5 Gy, and ileal tissues collected on day 6 following irradiation. Harvested samples were immediately fixed in buffered formalin, embedded in paraffin, and sectioned. Dehydration and antigen retrieval were performed before the tissues were incubated with rabbit anti-ANO1 (anoctamin 1) antibody at 1:500 dilution, followed by Alexa fluor conjugated secondary antibody, with 488 nm excitation and emission at 515 nm.
Intracellular Calcium and cAMP Measurements
Intracellular calcium levels were measured in isolated mouse small intestinal cells loaded with Fluo-8 AM dye and incubated for 45 minutes. Fluorescent images were captured with a scanning confocal microscope fitted with argon lasers with an excitation of 488 nm and emission of 515 nm wavelengths. Intracellular cAMP measurements were made on cell lysates from freshly isolated ileal epithelial cells using a cAMP direct immunoassay (Calbiochem, EMD Millipore, Billerica, Mass., USA)
Western Blot Analysis
Thirty micrograms of protein were resolved by electrophoresis through SDS-7% polyacrylamide gels. Blots were subsequently reacted with rabbit anti-ANO1 antibody at 1-2 ug/ml, followed by peroxidase-coupled secondary antibody at a 1:3000 dilution. Immunoreactive bands were visualized by enhanced chemiluminescence and autoradiography.
Results
The results, as shown in FIGS. 4-9, show that exposure to radiation results in a dose-dependent increase in Isc and a time-dependent increase in anion secretion in mouse small intestine. Irradiation also increases intracellular calcium levels but does not increase cAMP levels in ileal epithelial cells. Also, irradiation increases ANO1 expression levels in the brush border membrane of villous epithelial cells. Western blot analysis showed increased ANO1 protein levels in BBMV of ileal epithelial cells following irradiation, and increased ANO1 protein level in RBC membranes of mice that received irradiation.
The results show that ANO1 is an important transporter mediating the radiation-induced diarrhea. Also, ANO1 protein levels in RBC membrane increases with radiation exposure; therefore, ANO1 expression levels in RBC membrane can be used as a surrogate marker for acute gastrointestinal toxicity.

Example 3

The Use of Enzyme-Linked Immunosorbent Assay (ELISA) for Determining Ano1 Level

In a preferred embodiment, the ANO1 level is determined using the enzyme-linked immunosorbent assay (ELISA), which can be used to determine the level of ANO1 in both native and denatured conformations.

In one embodiment, procedures for performing ELISA are illustrated as follows:

A "capture" antibody raised against ANO1 is immobilized onto the surface of a polystyrene 96-well microtiter plate. The unbound areas of the wells are blocked with bovine serum albumin or casein to minimize background. A test sample with unknown quantity of ANO1 is applied to the wells, followed by the application of a "detection" antibody for binding to ANO1, thereby forming a ternary complex (The "detection" antibody should be directed against an epitope different from that for the "capture" antibody). Next, an enzyme-linked antibody that recognizes the "detection" antibody is added, and then the enzyme's substrate is added. The reaction produces a detectable signal, most commonly a color change, as a function of time, proportional to the concentration of the ANO1 present in the sample.

In one embodiment of the ELISA method, all steps utilize aqueous reagents. Also, at least two different, specific, antibodies against two different epitopes of ANO1 are used. Each step is followed by 2-3 washes with phosphate buffered saline (PBS) containing a non-ionic detergent to remove any residual proteins or antibodies that are not specifically bound. All steps are performed at room temperature (sample incubation can be at 37° C.). The ELISA method also requires a plate reader with the appropriate wavelength of visible light.

Table 1 lists reagents useful for determining ANO1 level in a sample using the ELISA method.

TABLE 1

| Reagents useful for ELISA |
|---|
| Chemicals |
| Sodium phosphate-monobasic |
| Sodium phosphate-dibasic |
| Sodium chloride |
| TWEEN ™ 20 |
| TRITON ™ X-100 |
| Bovine Serum Albumen |
| Non-fat dry milk |
| Casein |
| TMB peroxidase substrate |
| Hydrogen Peroxide (30% Soln) |
| Ethanol (200 proof) |
| Antibodies |
| EB 08600 |
| EB 08583 |
| ProSci 5419 |
| Aviva 42506 |
| HRP-anti rabbit |
| HRP-anti goat |

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A method of mitigating radiation toxicity in a human subject, who has undergone therapy with ionizing radiation, wherein the method comprises:
   (a) providing a blood sample from a subject who has been subjected to therapy with a predetermined dose of ionizing radiation;
   (b) determining anoctamin 1 expression level in the subject's blood sample; and
   (c) comparing the expression level determined in step (b) to a level of anoctamin 1 expression in the subject prior to the subject receiving the radiation therapy;
   wherein if the level of anoctamin 1 expression determined in (b) is greater than 105% of the anoctamin 1 expression level of the subject before the subject received the predetermined dose of ionizing radiation, then prescribing additional radiation at a dose lower than the predetermined dose or discontinuing radiation therapy; and
   if the level of anoctamin 1 expression determined in (b) is no greater than 105% of the anoctamin 1 expression level of the subject before the subject received the predetermined dose of ionizing radiation, then continuing the radiation therapy at the predetermined dose.

* * * * *